United States Patent [19]
von Recklinghausen

[11] 4,429,702
[45] Feb. 7, 1984

[54] APPARATUS FOR MEASUREMENT OF ACOUSTIC VOLUME

[75] Inventor: Daniel R. von Recklinghausen, Arlington, Mass.

[73] Assignee: Electro Audio Dynamics, Inc., Great Neck, N.Y.

[21] Appl. No.: 275,866

[22] Filed: Jun. 22, 1981

[51] Int. Cl.³ ............................................. G01N 29/00
[52] U.S. Cl. ...................................... 128/746; 73/585; 73/149
[58] Field of Search ..................... 73/585, 149, 290 V, 73/290 B; 128/746; 179/1 N

[56] References Cited

U.S. PATENT DOCUMENTS

| | | | |
|---|---|---|---|
| 3,237,451 | 3/1966 | Haeff | 73/149 |
| 3,540,275 | 11/1970 | Post et al. | 73/290 V |
| 4,079,198 | 3/1978 | Bennett | 73/585 |

*Primary Examiner*—Anthony V. Ciarlante
*Attorney, Agent, or Firm*—Holland, Armstrong, Wilkie & Previto

[57] ABSTRACT

Improvements are described for apparatus used in the measurement of acoustic admittance in ear canals including circuit means for permitting the measurement of relatively small acoustic volumes with an accuracy of better than one percent.

7 Claims, 8 Drawing Figures

$$Z_S = R_E + j\omega\left(L_E + L_{pe} + \cfrac{1}{\cfrac{1}{L_{ve}} - \omega^2 C_{pe}}\right)$$

$$Z_S = R_E + jx = R_E + j\omega L$$

$$L = L_E + L_{pe} + \cfrac{1}{\cfrac{1}{L_{ve}} - \omega^2 C_{pe}}$$

$$\frac{1}{L_{ve}} = \frac{1}{L - L_E - L_{pe}} + \omega^2 C_{pe}$$

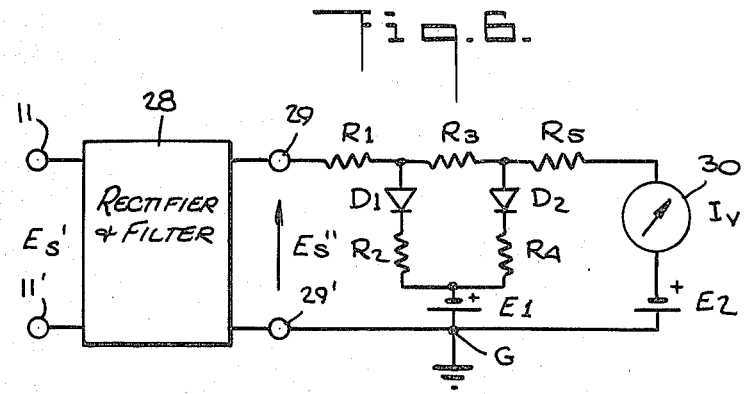
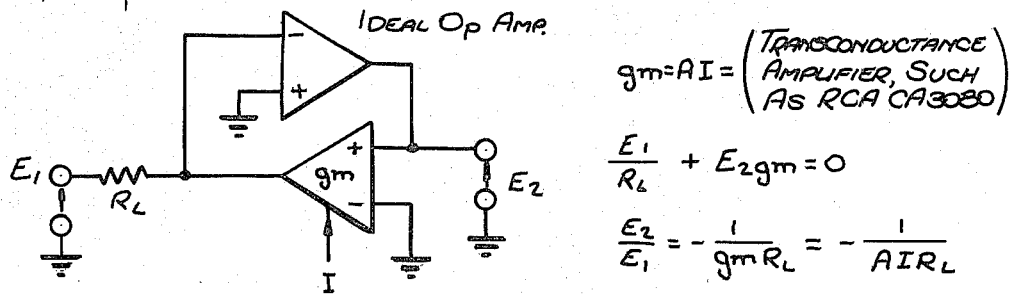
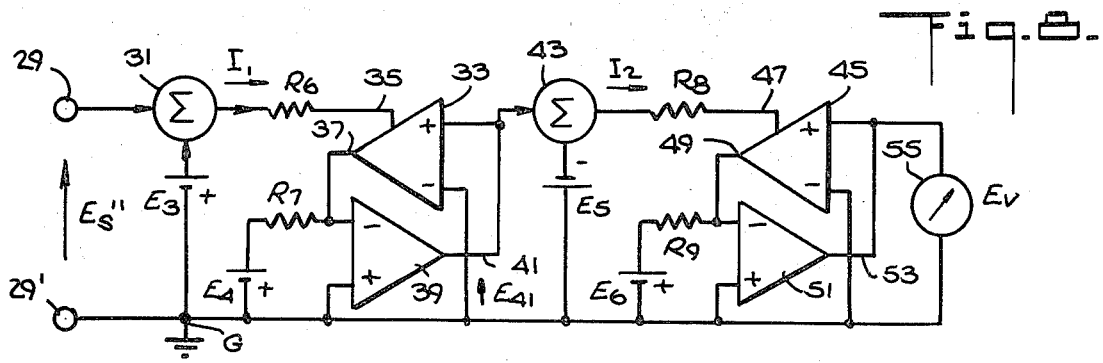

TABLE 1

$$I_1 = \frac{E_s'' - E_3}{R_6} \quad I_2 = \frac{E_{41} + E_5}{R_8} \quad E_{41} = -\frac{-E_4}{A_{33} I_1 R_7} \quad E_v = -\frac{-E_6}{A_{45} I_2 R_9}$$

$$E_v = \frac{E_6}{A_{45} R_9 \frac{E_5 + E_{41}}{R_8}} = \frac{E_6 E_8}{A_{45} R_9 \left(E_5 + \frac{E_4}{A_{33} I_1 R_7}\right)} = \frac{E_6 R_8}{A_{45} R_9 \left(E_5 + \frac{E_6 R_8}{A_{33} R_7 (E_s'' - E_3)}\right)} =$$

$$E_v = \frac{1}{\frac{A_{45} R_9}{E_6 R_8} \left(\frac{E_4 R_6}{A_{33} R_7}\right) \left(\frac{E_5 A_{33} R_7}{E_4 R_6} + \frac{1}{E_s'' - E_3}\right)} = \frac{1}{K_2 + \frac{1}{E_s - K_1}}$$

WHERE $K_1 = E_3$ and $K_2 = \frac{E_5}{E_4} \frac{R_7}{R_6} A_{33}$ and $\frac{A_{45} E_4 R_6 R_9}{A_{33} E_6 R_8 R_7} = 1$, $\quad \frac{\omega L v e}{K_0} = E_v$

APPARATUS FOR MEASUREMENT OF ACOUSTIC VOLUME

BACKGROUND OF THE INVENTION

The present invention relates to improvements in apparatus primarily designed to measure the acoustic impedance or admittance of structures. In particular, it relates to apparatus designed to measure these values for the human external auditory canal.

Previously, the measurement of the acoustic impedance or the measurement of the reciprocal acoustic admittance has typically involved the measurement of such quantities at relatively low frequencies where each acoustic element was believed to be relatively small compared to the wavelength of sound and thus could be treated as a lumped constant, such as mass or stiffness. This is similar to describing electrical structures which are measured having a value of capacitance or inductance rather than being part of distributed circuits such as transmission lines.

For example, the medical screening for certain ear ailments involves in part, the measurement of the physical volume of the outer ear canal, the measurement of the effective volume of the ear canal and of the middle ear volume with the eardrum not tensioned, and a measurement of the volume change when the patient is exposed to acoustic or other stimuli.

The measurement of such volumes involves the measurement of the acoustic characteristics of the volume having dimensions which are very small compared to the wavelength of sound and air at the test frequency. If this Volume V was sealed but subjected to a Volume change $\Delta V$ from some transducer, the resultant pressure change or sound pressure would be $p = \gamma \times P_o \times \Delta V/V$ where $P_o$ is the ambient air pressure (near $10^5$ N/meter square at sea level) and $\gamma$ is the adiabatic coefficient (near 1.4 for air). If, for example, the relative volume change or $\Delta V/V$ equal to 0.001% peak to peak, the resultant sound pressure level within that volume would be approximately 88 dB rms with respect to the standard reference level of 0.0002 dynes/cm$^2$.

Practical instruments for the measurement of such small volumes of the ear canal amounting to values ranging between 0.2 and 5 cm$^3$ have involved certain compromises which had to be reached because these volumes are comparable and perhaps even smaller than the volumes of the smallest miniature electroacoustic transducers available. Consequently, all these transducers had to be positioned outside the actual ear canal and be coupled to the ear canal by an ingenious arrangement of various concentric or separate tubes, ultimately terminating at a common seal which was positioned either on the surface of the entrance to the ear canal or within the entrance of the ear canal itself.

In practice also, at least two transducers had been involved, one of them, a microphone effectively measuring the sound pressure level and a second transducer acting as a generator of the volume displacement. In prior art, the output of the microphone would be measured after being amplified in a selective tuned circuit tuned to the measuring frequency, the output of that filter rectified and compared to a referenced voltage to provide a signal which would ultimately control the amplification of an electronic stage interspersed between a fixed frequency oscillator and the volume changing acoustic generator.

The signal at the input to the volume changing transducer often in the form of a miniature magnetic headphone-type of unit, would be measured by means of a voltmeter sensitive to alternating voltages. This voltmeter would be calibrated directly in terms of the acoustic volume connected to both the microphone and the other transducer.

These test probes containing both the microphone and the volume changing transducer have appeared in many forms, however all of these forms being ingenious arrangements so that the measurement of the acoustic volume was directly proportional to the aforesaid meter reading. Various tubes, be they concentric or placed side by side, connected to both microphone and the other transducer were used and these typically were of relativly small diameter and consequently, very easily contaminated by dirt and delicate to handle.

A second major disadvantage of these types of volume measuring probes has been their inaccuracy in maintaining linear relationship between the volume measured and the voltage applied to the transducer.

In order to avoid certain of the contamination and handling problems, probes have been designed which use a common duct leading to the end of the probe, however these probes have suffered not only from the presence of the added volume entering into the measurements, but also from the fact that resonance effects and other phenomena have caused a severe decrease in the possible accuracy of measurement.

Accordingly, the object of the apparatus that is about to be described is to overcome these disadvantages and to permit repeatable construction as well.

Other and further objects of the present invention will become apparent upon an understanding of the illustrative embodiments about to be described or will be indicated in the appended claims, and various advantages not referred to herein will occur to one skilled in the art upon employment of the invention in practice.

A preferred embodiment of the invention has been chosen for purposes of illustration and description and is shown in the accompanying drawings, forming a part of the specification wherein:

FIG. 6 is a schematic representation of a circuit which provides linear indication.

FIG. 7 shows the insertion of a transconductance amplifier into the feedback path of an ideal operational amplifier fed by a voltage source by way of a load resistor and shows relationships of input voltage, output voltage and control current.

FIG. 8 is a schematic representation for providing accurate measurement by analog computation of the various quantities involved.

DESCRIPTION OF THE PREFERRED EMBODIMENTS

Figure 1:
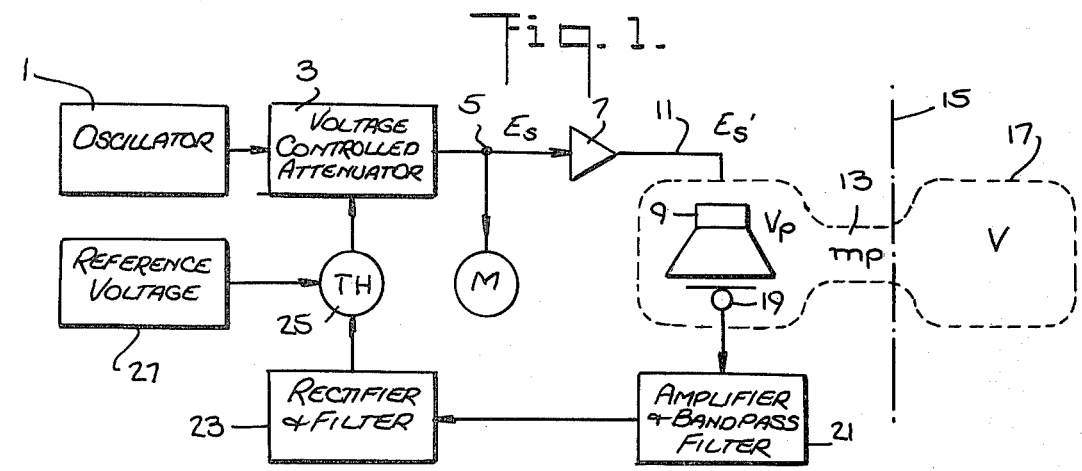
FIG. 1 is a block diagram and schematic representation of the apparatus.

In FIG. 1 a block diagram of a typical circuit largely of prior art is shown as adapted for the measurement of an acoustic volume, V. Referring to FIG. 1, an oscillator 1 having a fixed frequency of typically 226 Hz provides the input signal to a voltage controlled attenuator 3 the output of which 5 provides signal voltage $E_s$ fed by way of an optional further amplifier 7 to the input terminals 11 of the electroacoustic transducer 9 located inside of a probe housing 13 which makes contact with the volume, V, represented by an envelope 17 at the interface plane 15. Also located inside probe 13 is a microphone 19 the electrical output of which is amplified in an amplifier and bandpass filter 21 which feeds rectifier and filter circuit 23 the output of which feeds a summing device 25 having as its second input a reference voltage 27 threshhold. The Summing device 25 controls the gain of the voltage controlled attenuator 3. Thus, the reference voltage 27 in effect provides for a constant sound pressure level existing at microphone 19 which will cause the gain of attenuator circuit 3 to be reduced as volume V changes. Consequently, the driving voltage through transducer 9 will tend to vary depending upon the acoustical environment seen by microphone 19 and transducer 9.

For the purpose of the following description, it will be assumed that transducer 9 is linear and the change in volume $\Delta V$ of transducer 9 due to a signal voltage $E_s$, due to voltage existing at terminal pair 11 is proportional at the fixed frequency provided by oscillator 1. Methods for compensating and correcting the nonlinear transfer characteristics of transducers are described in my co-pending application Ser. No. 273,742 entitled Apparatus for Improving Linearity of Electromechanical Transducers and filed on June 15, 1981.

A meter M connected to node 5 measuring the signal voltage $E_s$ is usually connected to terminal pair 11 and measures signal voltage $E_s'$ and should ideally provide an indication proprotional to size of volume V.

Figure 2:
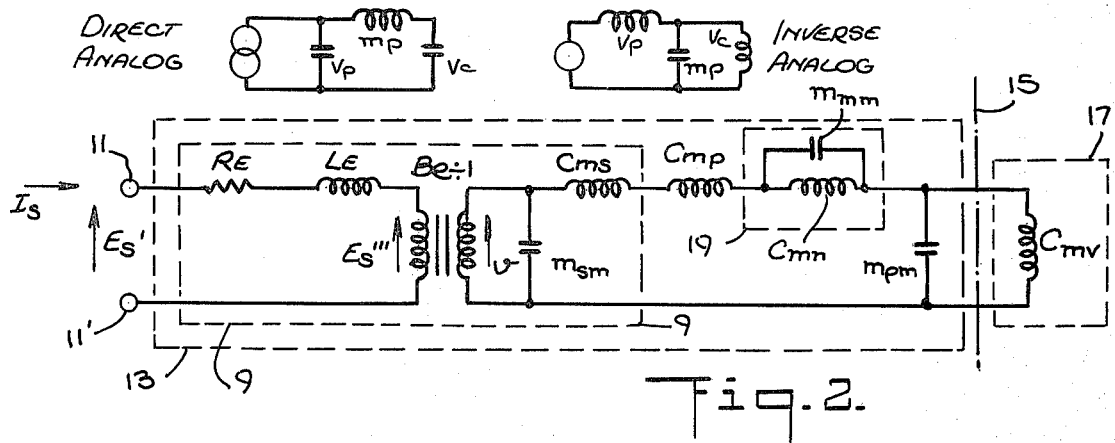
FIG. 2 is a schematic representation of the acoustical and electrical measuring circuit.
Figure 3:
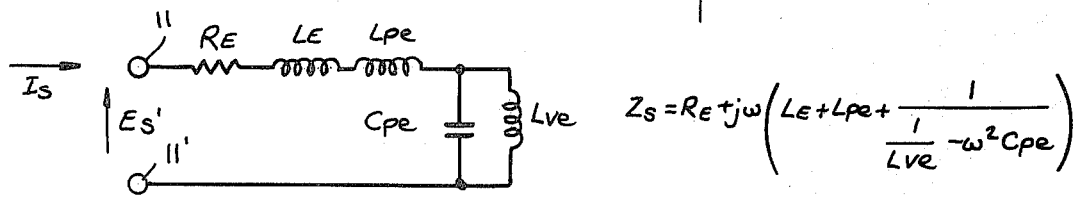
FIG. 3 is a simplified schematic representation.
Figure 4:
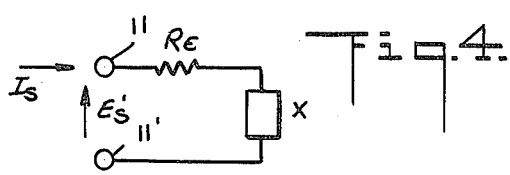
FIG. 4 is a further simplification of the schematic representation.

By means of equivalent circuits of FIGS. 2, 3 and 4, it will be shown that voltages cannot be exactly proportional to volume V even allowing for an ideal perfect linearity of transducer 9.

Referring to FIG. 2, analysis is made as if transducer 9 is located inside of probe 13 which also houses microphone 19. It is assumed here that the transducer is of the electromagnetic variety in which the velocity of the diaphragm is proportional to the combination of flux density B and effective length 1 which may be represented by an ideal transformer having at its input voltage $E_s'''$ and an output velocity v. Mechanically, this transducer 9 also has a moving mass $M_{sm}$ and a diaphragm compliance $C_{ms}$. Its electrical terminals have its winding resistance, $R_e$ connected in series with its inductance $L_e$ providing the input voltage for such ideal transformer having a turns ratio B1:1.

On the output side of the transformer, represented here as a mechanical circuit, are the mechanical mass of the transducer diaphragm $M_{sm}$ its compliance $C_{ms}$ which in turn are connected to the microphone 19, with its compliance $C_{mm}$ and microphone mass $M_{mm}$. Also operating at the same velocity is the input of the residual volume of the probe having a compliance $C_{mp}$ coupled to the neck of the probe which in turn has a mechanical mass $M_{pm}$ to interface plane 15 to the volume V represented by 17 having a compliance $C_{mv}$.

This rather complex acoustical circuit can be simplified for the purposes of measurement at a single low frequency. Thus, one can neglect the higher frequency resonances caused by diaphragm mass of both transducers 9 and 19 and one can replace the mechanical and electro-acoustical quantities represented by these various items above by the simplified circuit of FIG. 3 in which all of the summed and replacement quantities have been expressed as electrical quantities.

In FIG. 3, input terminals 11 and 11' with input current $1_s$ and input signal voltage $E_s'$ are identical to those of FIG. 2 as are the electrical quantities of transducer 9 such as winding resistance $R_e$ and electrical inductance $L_e$. The electrical quantity $L_e$ is the equivalent of the residual compliances of microphone 19, the effects of the combination of mass $M_{sm}$ and compliance of the transducer 19 $C_{mp}$, as well as the residual compliance of probe volume $V_p$ having an effective compliance $C_{mp}$. The neck mass of probe 13 is represented as an electrical capacitance $C_{pe}$ and the volume 17 having a compliance $C_{mv}$ is represented as an electrical quantity $L_{ve}$. It may be appreciated that it is desired to measure this effective electrical quantity $L_{ve}$ using nothing but terminals 11 and 11'.

In FIG. 4, a further simplification has been made where all reactive elements of FIG. 3 are replaced by a single reactance X in series with a resistance $R_e$ with input terminals 11 and 11' the same as in FIGS. 2 and 3.

Figure 5:
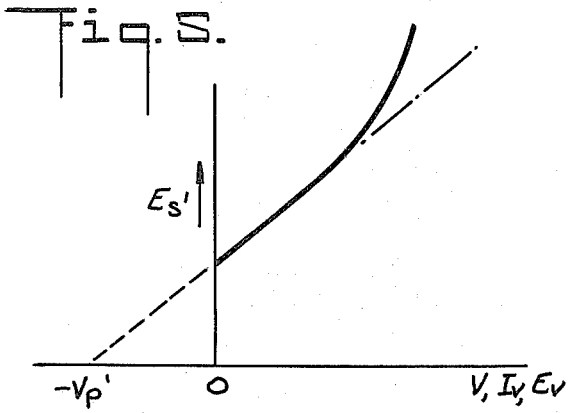
FIG. 5 illustrates the relationship between the electrical signal and the volume signal level and other measured quantities.

In FIG. 5 is shown a typical relationship between the electrical voltage $E_s'$ with respect to volume V using unmarked linear scales with 0 marking the values of zero.

It will be seen that when the external volume is 0 or the neck of the probe is blocked at interface surface 15, it is not necessary that signal voltage $E_s'$ is necessarily 0. In prior art, using a complex arrangement of probe tubes, a signal voltage $E_s'$ near 0 was obtained with a blocked probe. Therefore, prior practical circuits and probes have not been capable of measuring relatively small volumes V accurately.

In FIG. 5 it can also be observed that the dash line intersects the 0 voltage line at some equivalent negative value $-V_p'$ which is the effective probe volume of the equivalent probe circuit. It is, of course, desired to make this effective value to be as reasonably small as practical. Furthermore, it will be seen in FIG. 5, that the relationship of signal voltage $E_s'$ and volume V is nonlinear above a certain critical value of volume V.

It may be appreciated at this point that this departure from proportionality is caused by the air mass $M_{pm}$ of FIG. 2 as represented as an electric quantity $C_{pe}$ in FIG. 3 approaching resonance with the equivalent electrical inductance $L_{ve}$ representing the volume V to be measured.

It has been discovered that probes with relatively wide necks can be designed to have a resonance with volume V and neck air mass $M_p$ of the probe 13 always above the test frequency. Then the curve of FIG. 5 is repeatable and therefore, the nonlinear circuit shown in FIG. 6 could be developed to compensate for effects of such resonance. Referring to FIG. 6, input signal $E_s'$ appearing at terminals 11 and 11' is rectified by means of precision rectifier 28 whose output voltage $E_s''$ is available at terminals 29 and 29' with terminal 29' connected to ground G. The nonlinear curve of FIG. 5 is compensated for to produce a signal current $I_v$ in meter 30 by a nonlinear network consisting of resistors $R_1$ and $R_5$ and diodes $D_1$ and $D_2$ with compensating batteries $E_1$ and $E_2$ connected schematically as shown. The residual volume $-V'$ causes a meter 30 to read a current of 0 when compensating voltage source $E_2$ is adjusted to be equal to voltage $E_s''$ when volume V is equal to 0 or a blocked probe exists.

Referring back to FIG. 3, it can be seen that the reactive part of $Z_s$ is equal to the sum of two positive reactances corresponding to the equivalent inductances of the probe microphone, the probe itself, plus the transformed equivalent volume of electrical inductance of transducer 9 plus the unknown inductance equal to the equivalent inductance of the volume to the measured $L_{ve}$ and a negative reactance, the mass of the air in the neck connected in parallel with it. The electrical resistance corresponds to the circuit losses which can be compensated as shown in my above referred to copending application. This loss is relatively small.

The circuit of FIG. 8 is capable of performing the necessary analog multiplication functions to exactly compensate for the effects of mass $M_p$ or the electrical capacitor $C_{pe}$ at the fixed probe frequency.

The circuit of FIG. 7 helps to illustrate matters in providing the necessary mathematical function. An ideal operational amplifier $A_0$ with its + input grounded has a voltage source $E_1$ connected through a resistor $R_L$ to its − input. The output of a transconductance amplifier $g_m$ which receives its input voltage from the output $E_2$ of the operational amplifier $A_0$ is also connected to the − input. The operational transconductance amplifier, such as RCA type CA 3080, has a transconductance $g_m$ which is equal to the product of a factor A, designed into the amplifier and a current 1 provided as a bias current for said amplifier $A_0$. Consequently, the output voltage to input voltage ratio $E_2/E_1$ is equal to $-1/g_m R_L$ which is equal to $-1/A \times I \times R_L$. This circuit is capable of performing the reciprocal function required to solve for the exact measurement of an electrical measurement of an electrical quantity exactly proportional to volume V. Referring back to FIG. 2 the purpose of microphone 19 is to maintain constant sound pressure level within the probe 13. This may be represented by a constant flow of equivalent current through block 19 which will cause a voltage drop to appear across inductance $C_{mp}$ and the parallel combination of neck mass $M_{pm}$ volume under test $C_{mv}$, both of which are connected in parallel. The above elements are in series with the equivalent compliance of the transducer 9 and the remainder of its electrical circuit as transformed by the ideal transformer B1:1.

In a simplified form, in FIG. 3, the whole system is represented as an impedance consisting of the equivalent inductance multiplied by the radian frequency plus a resistance. The resistance may be neglected for the initial purposes of computation and the necessary equations are shown in FIG. 4 requiring a form of subtraction, summation and double inversion of the total quantities.

The circuit of FIG. 3 is fairly complex to analyze, however, the equations of Table 1 indicate that this circuit is indeed capable of performing the above requirements of FIG. 4. The circuit of FIG. 8 consists of input terminals 29 and 29' receiving a precision rectified and filtered input voltage $E_s''$ which in turn feeds a summing junction 31 which as second input receives reference voltage $E_3$. The output of summing junction 31 by way of resistor $R_6$ provides input current, $I_1$ of transconductance amplifier 33, such current being fed into the control terminal 35. This transconductance amplifier 33 is the feedback impedance of feedback current source of operational amplifier 39 which also receives into its − input a second negative voltage $E_4$ by way of resistor $R_7$. The output voltage at output terminal 41 of operational amplifier 39 provides voltage $E_{41}$ which is one input to summing junction 43 which receives also a second input reference voltage $E_5$ producing a total output voltage which by way of resistor $R_8$ provides input current $I_2$ into reference junction 47 of transconductance amplifier 45. This transconductance amplifier 45 with its output 49 connected to the minus terminal of operational amplifier 51 provides the feedback signal and the input signal being provided from the minus terminal of the referenced voltage $E_6$ by way of resistor $R_9$. The output, $S_3$ of operational amplifier 51 provides output voltage $E_v$ into meter circuit 55. Referring now to FIG. 4, in order to measure an equivalent inductance $L_{ve}$ proportional to volume V, a dual inversion is required and here in Table 1, the output voltage $E_v$ is in fact, directly proportional to the measurement of voltage $E_s'$. The constant $K_1$ and $K_2$ as used as constants in Table 1, are being used to simplify some of the mathematics involved.

These above circuits now permit the measurement of relatively small acoustic volumes to accuracies previously thought to be impractical for equipment of that nature without substantially increasing the complexity. Whereas, in the past, accuracies of ±5% were the best achievable over the range of 0.2 and 5 cm$^3$, circuits of the present invention can now perform these measurements to an accuracy of better than 1%.

It is, of course, possible to perform the mathematical and electrical corrections of signals as shown in FIG. 6 by means other than analog circuits. For example, the performance of FIG. 6 could be achieved by taking the output of precision rectifier and filter 28 at its terminals 29 and 29', performing an analog to digital conversion then providing a lookup table which provides the necessary nonlinear functions as function of measured voltage, then subtracting the value found in that lookup table to provide a digital output signal which then can be read directly by digital indicating devices, such as customarily used.

Similarly, the circuit of FIG. 8 could be implemented by digital means in exactly the same fashion using an analog-to-digital converter connected to terminals 29 and 29' and performing the calculations of the equivalent of that circuit by subtraction, addition and inverting of digital numbers. Consequently, similar accuracies may be provided.

As various changes may be made in the form, construction and arrangement of the parts herein without sacrificing any of its advantages, it is to be understood that all matter herein is to be interpreted as illustrative and not in a limiting sense.

Having thus described my invention, I claim:

1. In an apparatus for measuring acoustic volumes in human ears utilizing a hollow ear probe housing a sound transducer in combination with a microphone for transmitting into and receiving sound signals from said acoustic volume and an electrical circuit for feeding a signal to said transducer and generating an output from said microphone proportional to said volumes the improvement comprising a compensating nonlinear network incorporated in said electrical circuit and including elements for offsetting the nonlinearities in the combination of said probe and said transducer and said microphone for producing linear measurements of volume with improved accuracy, said probe having a wide-mouthed coupling with the measured ear canal with the resonance volume of the said acoustic volume and the probe volume being above that of the frequency of the signal being applied to the sound transducer.

2. The apparatus as claimed in claim 1 in which the nonproportionalities comprise the compliance of the residual volume of the probe, the equivalent mechanical mass of the probe, and the compliance of the acoustic volume.

3. The network as claimed in claim 1 in which said compensating nonlinear network comprises interconnected resistors and diodes plus one or more interconnected voltage sources.

4. The network as claimed in claim 1 in which said compensating nonlinear network comprises a voltage source connected in series with a resistance and a shunt connected across a portion of said resistance comprising a serially connected diode, resistance and voltage source.

5. The apparatus as claimed in claim 1 where the compensating network comprises a circuit including an operational transconductive amplifier.

6. The apparatus as claimed in 5 in which said operational transconductance amplifier performs a reciprocal function required to solve the measurement of an electrical quantity proportional to the acoustic volume V.

7. The network as claimed in claim 1 where the nonlinearity results from a circuit impedance $Z_s$ comprising a resistive component $R_e$ representing the transducer winding resistance plus a reactive component comprising approximately $$j\omega \left( L_e + L_{pe} + \frac{1}{\frac{1}{L_{ve}} - \omega^2 C_{pe}} \right)$$

as defined in the above description where $L_e$ is the equivalent electrical inductance of the residual compliance of the microphone, and $L_{pe}$ is the equivalent electrical inductance of the air mass of the air in and $L_{ve}$ is the equivalent electrical inductance representing the acoustic volume to be measured and $C_{pe}$ is the equivalent electrical capacitance of the air mass of the air in the acoustic volume.

* * * * *